United States Patent
Rosener et al.

(10) Patent No.: US 9,884,298 B2
(45) Date of Patent: *Feb. 6, 2018

(54) FRAGRANCE NEBULIZER WITH DRAINAGE SYSTEM

(71) Applicant: ScentAir Technologies, LLC, Charlotte, NC (US)

(72) Inventors: Martin John Rosener, Fort Mill, SC (US); Robert David Blaylock, Tega Cay, SC (US); John Thurston Chandler, Charlotte, NC (US); Garrett Michael Sherman, Charlotte, NC (US)

(73) Assignee: SCENTAIR TECHNOLOGIES, LLC, Charlotte, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/332,681

(22) Filed: Oct. 24, 2016

(65) Prior Publication Data

US 2017/0036177 A1    Feb. 9, 2017

Related U.S. Application Data

(60) Division of application No. 14/510,800, filed on Oct. 9, 2014, now Pat. No. 9,474,820, which is a (Continued)

(51) Int. Cl.
*B01F 3/04* (2006.01)
*A01M 1/20* (2006.01)
(Continued)

(52) U.S. Cl.
CPC ....... *B01F 3/04021* (2013.01); *A01M 1/2044* (2013.01); *A61L 9/12* (2013.01);
(Continued)

(58) Field of Classification Search
CPC ... B05B 7/2405; B05B 7/2408; B05B 7/2429; B05B 7/2402; B05B 7/2424;
(Continued)

(56) References Cited

U.S. PATENT DOCUMENTS

| 3,958,724 | A * | 5/1976 | Ordway | B05B 9/0403 137/455 |
| 8,857,735 | B2 * | 10/2014 | Rosener | A01M 1/2044 239/124 |
| 9,474,820 | B2 * | 10/2016 | Rosener | A01M 1/2044 |

* cited by examiner

*Primary Examiner* — Christopher Kim
(74) *Attorney, Agent, or Firm* — Kilpatrick Townsend & Stockton LLP (57) ABSTRACT

A device for generating a scented mist of an atomized liquid fragrance oil includes an atomizer complex, a reservoir assembly, a drainage tube, and a vacuum tube. The atomizer complex can atomize the liquid fragrance oil into a scented mist and deliver the scented mist to air outside of the atomizer complex, where the liquid fragrance oil the fragrance oil that is not atomized into the scented mist delivered to the air outside of the atomizer complex includes collected oil that is collected and drained to a reservoir assembly. A drainage tube extends from a bottom area of the atomizer complex into the liquid fragrance oil. The device can filter the liquid fragrance oil in the reservoir assembly and the collected oil from the atomizer complex that drained down the drainage tube. The vacuum tube can suction the filtered liquid fragrance oil and the collected oil into the atomizer complex for atomization.

9 Claims, 9 Drawing Sheets

Related U.S. Application Data continuation of application No. 12/768,444, filed on Apr. 27, 2010, now Pat. No. 8,857,735.

(60) Provisional application No. 61/252,558, filed on Oct. 16, 2009.

(51) Int. Cl.
*A61L 9/12* (2006.01)
*A61L 9/14* (2006.01)
*B05B 7/24* (2006.01)
*B05B 15/00* (2006.01)
*B01F 5/02* (2006.01)
*B01F 15/02* (2006.01)

(52) U.S. Cl.
CPC ............ *A61L 9/145* (2013.01); *B01F 5/0206* (2013.01); *B01F 15/0248* (2013.01); *B05B 7/2424* (2013.01); *B05B 7/2427* (2013.01); *B05B 7/2435* (2013.01); *B05B 7/2437* (2013.01); *B05B 7/2489* (2013.01); *B05B 15/005* (2013.01); *A61L 2209/131* (2013.01); *A61L 2209/133* (2013.01); *A61L 2209/134* (2013.01); *A61L 2209/14* (2013.01); *B01F 2215/009* (2013.01)

(58) Field of Classification Search
CPC ... B05B 7/2427; B05B 7/2435; B05B 7/2437; B05B 7/2489; B05B 15/005; A61L 9/015; A61L 9/04; A61L 9/12; A61L 9/14; A61L 2209/10; A61L 2209/13; A61L 2209/131; A61L 2209/133; A61L 2209/134; A61L 2209/14; A61L 9/145; A01M 1/20; A01M 1/2022; A01M 1/2027; A01M 1/2044; B01F 3/04021; B01F 5/0206; B01F 15/0248; B01F 2215/009
USPC ................. 239/124, 126, 127, 340–343, 346
See application file for complete search history.

TOP VIEW

- 240
- 404
- 235

SIDE VIEW

- 401
- 408
- 406
- 404
- 240
- 240
- 235
- 408
- 408

ESCAPING AEROSOL

NON-ATOMIZED LIQUID
DRAINS DOWN INSIDE
OF TUBE 230

- 407
- 409A
- 409B
- 486
- 220
- 488
- 230

MIX OF NON-ATOMIZED
AND FRESH OIL
490

LIQUID IN BOTTLE
210

SCREEN HOUSING, 492
FILTER SCREEN, 494

SMALL HOLES IN SCREEN HOUSING, 498,
ALLOWING RECIRCULATION, 496

FRAGRANCE NEBULIZER WITH DRAINAGE SYSTEM

CROSS-REFERENCE TO RELATED APPLICATIONS

This application is a continuation (and claims the benefit of priority under 35 USC 120) of U.S. Ser. No. 14/510,800, filed Oct. 9, 2014, which is a continuation of U.S. Ser. No. 12/768,444, filed Apr. 27, 2010, which claims the benefit to U.S. Provisional Application Ser. No. 61/252,558, entitled "Fragrance Nebulizer with Drainage System," filed on Oct. 16, 2009, the disclosures of each of which are incorporated by reference in their entirety for all purposes.

TECHNICAL FIELD

This invention relates to scent and fragrance delivery systems.

BACKGROUND

Products can be developed to deliver scents or aromas in a commercial environment, such as in a retail environment. The scents can improve a customer's perception of the store, the environment and the products, and can make the customer want to revisit the store to buy something. Scents and systems can be customized to reflect and complement various brands or environments.

SUMMARY

Generally, embodiments feature scent delivery systems and scent delivery methods. A scent delivery system features an atomizer complex to atomize a liquid fragrance oil into a scented mist and deliver the scented mist to air outside of the atomizer complex, where the fragrance oil that is not atomized into the scented mist delivered to the air outside of the atomizer complex includes oil that is collected and drained to a reservoir assembly. The system includes a drainage tube extending from a bottom area of the atomizer complex into the liquid fragrance oil, where the drainage tube is configured to drain the collected oil from the atomizer complex down the drainage tube into the liquid fragrance oil in the reservoir assembly. The system has a vacuum tube configured to suction the liquid fragrance oil and the collected oil from the reservoir assembly into the atomizer complex for the atomization. The system includes a funnel-shaped structure located on the bottom area of the atomizer complex, where the funnel-shaped structure is configured to use impaction to coalesce a first portion of atomized particles back into liquid form for forming the collected oil, where a second portion of the atomized particles includes the scented mist that is delivered to the air outside of the atomizer complex.

These and other embodiments can optionally include one or more of the following features. The reservoir assembly can contain a supply of the liquid fragrance oil for the scent delivery system. The drainage tube can include the vacuum tube inside of the drainage tube that extends along a longitudinal length down the drainage tube, and the drainage tube can be configured to at least contact a level of the liquid fragrance oil in the reservoir assembly. The drainage tube and the vacuum tube can be arranged to extend along a longitudinal length down into the reservoir assembly, and both the drainage tube and the vacuum tube can be configured to at least contact a level of the liquid fragrance oil in the reservoir assembly. The drainage tube and the vacuum tube can be arranged to be located substantially in parallel with one another. The atomizer complex can include an air inlet structure to receive pressurized air, an oil intake assembly, and a venturi chamber inside of the atomizer complex. The vacuum tube can be coupled to the oil intake assembly that leads to the venturi chamber. The scent delivery system can be configured to receive pressurized air through the air inlet structure to generate a first pressure area in the venturi chamber that is lower than a second pressure area in the reservoir assembly so that the liquid fragrance oil in the reservoir assembly is suctioned into the vacuum tube and to the venturi chamber. The atomizer complex can be configured to receive the collected oil from the reservoir assembly through the vacuum tube into the atomizer complex for the atomization, and utilize a pressurized air flow to atomize at least a portion of the received collected oil into the scented mist. The funnel-shaped structure can include a wide end and a tapered end, for which the wide end can be positioned on the bottom area of the atomizer complex, the vacuum tube can be threaded through the funnel-shaped structure, the drainage tube can be configured to receive the tapered end of the funnel-shaped structure, the funnel-shaped structure can include holes in the funnel-shaped structure, and the funnel-shaped structure can be configured to collect the collected oil and drain the collected oil through the holes in the funnel-shaped structure and to the drainage tube at the tapered end of the funnel-shaped structure. The atomizer complex can be configured so that the first portion of atomized particles in the atomizer complex impacts an interior area of the atomizer complex. Most of the first portion of atomized particles can have a momentum that is sufficient to be unable to change direction and escape to the air outside the atomizer complex. The scent delivery system can be configured to utilize a virtual impaction to deliver the scented mist to air outside of the atomizer complex. The first portion of the atomized particles can include large particles and the second portion of the atomized particles can include small particles. The scent delivery system can be configured to have an airstream to send the small particles to the air outside of the atomizer complex, and the virtual impaction can utilize a momentum of the large particles to remove the large particles out of the airstream that sends the small particles to the air outside of the atomizer complex. The scent delivery system can be configured to utilize a physical impaction to form the collected oil by directing the large particles to crash into a solid surface at least within the atomizer complex. The atomizer complex can include an output nozzle to deliver the scented mist to the air outside of the atomizer complex. The reservoir assembly can be configured to be sealed for transport or shipping to prevent a loss of liquid fragrance oil from the scent delivery system. The collected oil that drains into the reservoir assembly can include odor notes that are heavier than odor notes of the scented mist.

Other embodiments include an apparatus for a fragrance nebulizer with a drainage system. The apparatus includes an atomizer complex to atomize a liquid fragrance oil into a scented mist and deliver the scented mist to air outside of the atomizer complex, where the fragrance oil that is not atomized into the scented mist delivered to the air outside of the atomizer complex includes collected oil that is collected and drained to a reservoir assembly. The apparatus includes a drainage tube that is configured to extend from a bottom area of the atomizer complex into the liquid fragrance oil, where the drainage tube is configured to drain the collected oil from the atomizer complex down the drainage tube into the liquid fragrance oil in the reservoir assembly. The apparatus includes a vacuum tube configured to suction the liquid fragrance oil and the collected oil from the reservoir assembly into the atomizer complex for the atomization, and one or more pressure equalization holes in the drainage tube to equalize a first pressure in the drainage tube with a second pressure in the reservoir assembly.

These and other embodiments can optionally include one or more of the following features. The reservoir assembly can contain a supply of the liquid fragrance oil for the scent delivery system. The drainage tube can include the vacuum tube inside of the drainage tube that extends along a longitudinal length down the drainage tube, and the drainage tube can be configured to at least contact a level of the liquid fragrance oil in the reservoir assembly. The drainage tube and the vacuum tube can be arranged to extend along a longitudinal length down into the reservoir assembly, and the drainage tube and the vacuum tube can be configured to at least contact a level of the liquid fragrance oil in the reservoir assembly. The vacuum tube can be integrated within the drainage tube. The one or more pressure equalization holes can be positioned above a maximum level of the liquid fragrance oil in the reservoir assembly. The atomizer complex can include a funnel-shaped structure located on the bottom area of the atomizer complex, where the funnel-shaped structure can include a wide end and a tapered end. The wide end can be positioned on the bottom area of the atomizer complex, the vacuum tube can be threaded through the funnel-shaped structure. The drainage tube can be configured to receive the tapered end of the funnel-shaped structure, the funnel-shaped structure can include holes in the funnel-shaped structure, and the funnel-shaped structure can be configured to collect the collected oil and drain the collected oil through the holes in the funnel-shaped structure and to the drainage tube at the tapered end of the funnel-shaped structure. The apparatus can include one or more pressure equalization holes in the funnel-shaped structure to equalize a first pressure in the drainage tube with a second pressure in the reservoir assembly. The atomizer complex can be configured to use impaction to coalesce a first portion of atomized particles back into liquid form for forming the collected oil, where a second portion of the atomized particles can include the scented mist that is delivered to the air outside of the atomizer complex. The apparatus can be configured to recirculate the collected oil that drains into the reservoir assembly back into the vacuum tube and to the atomizer complex for re-atomization. The drainage tube can be configured to extend below the level of the liquid fragrance oil in the reservoir assembly. An area near a terminal end of the drainage tube can include a filter screen or a semipermeable membrane inside of the drainage tube. The vacuum tube can be configured to contact at least a top portion of the filter screen or the semipermeable membrane. The filter screen or the semipermeable membrane can be configured to filter the liquid fragrance oil in the reservoir assembly and the collected oil from the atomizer complex that drained down the drainage tube. The vacuum tube can be further configured to suction the filtered liquid fragrance oil and the collected oil back into the atomizer complex for atomization. Each of the one or more pressure equalization holes in the drainage tube can include a valve that is configured to seal the respective pressure equalization hole in a condition where the apparatus tips beyond a threshold degree away from a vertical position.

Some embodiments include a device for generating a scented mist of an atomized liquid fragrance oil. The device includes an atomizer complex to the atomize liquid fragrance oil into a scented mist and deliver the scented mist to air outside of the atomizer complex, where the fragrance oil that is not atomized into the scented mist delivered to the air outside of the atomizer complex includes collected oil that is collected and drained to a reservoir assembly. The device includes a drainage tube extending from a bottom area of the atomizer complex into the liquid fragrance oil, where the drainage tube includes a vacuum tube inside of the drainage tube that extends along a longitudinal length down the drainage tube. The drainage tube is configured to at least contact a level of the liquid fragrance oil in the reservoir assembly. The drainage tube is configured so that the collected oil from the atomizer complex drains down the drainage tube into the liquid fragrance oil in the reservoir assembly. The device is configured to filter the liquid fragrance oil in the reservoir assembly and the collected oil from the atomizer complex that drained down the drainage tube. The vacuum tube is configured to suction the filtered liquid fragrance oil and the collected oil in the reservoir assembly into the atomizer complex for atomization.

These and other embodiments can optionally include one or more of the following features. The device can include the reservoir assembly to contain a supply of the liquid fragrance oil for the device. Except for the atomized liquid fragrance oil that is delivered into the air as the scented mist, the device can be configured to constantly recirculate the oil in the device so that the oil remaining in the device is constantly filtered. The drainage tube can be configured to surround sidewalls of the vacuum tube. The drainage tube can be configured to extend below the level of the liquid fragrance oil in the reservoir assembly. An area near a terminal end of the drainage tube can include a filter screen or a semipermeable membrane inside of the drainage tube. The filter screen can be covered by a filter housing. The filter screen or the semipermeable membrane can separate a first mixture of oil inside the drainage tube from the liquid fragrance oil in the bottle. The filter housing can include holes to allow a second mixture of liquid oil located above the filter housing to travel underneath the filter housing and to be filtered by the filter screen before being suctioned into the vacuum tube. The second mixture of liquid oil above the filter housing can include non-atomized liquid oil and the collected oil. The second mixture liquid oil above the filter housing may be primarily the collected oil. The vacuum tube can be configured to contact at least a top portion of the filter screen or the semipermeable membrane. The filter screen or the semipermeable membrane can be configured to filter the liquid fragrance oil in the reservoir assembly and the collected oil from the atomizer complex that drained down the drainage tube into the reservoir assembly. The vacuum tube can be configured to suction the filtered liquid fragrance oil and the collected oil back into the atomizer complex for the atomization. The holes for the filter housing can be located through the filter housing and at an outsider perimeter area of the filter screen. The holes for the filter housing can be one-way valves.

Some embodiments feature a method for delivering a scented mist of atomized liquid fragrance oil. The method involves atomizing a liquid fragrance oil into a scented mist with an atomizer complex, delivering the scented mist to air outside of the atomizer complex, and collecting and draining collected oil into a reservoir assembly. The fragrance oil that is not atomized into the scented mist delivered to the air outside of the atomizer complex includes the collected oil that is collected and drained to the reservoir assembly. A drainage tube is configured to extend from a bottom area of the atomizer complex into the liquid fragrance oil, where the drainage tube is configured so that the collected oil from the atomizer complex drains down the drainage tube into the liquid fragrance oil in the reservoir assembly. The method involves filtering the liquid fragrance oil in the reservoir assembly, and suctioning, with the vacuum tube, the filtered liquid fragrance oil into the atomizer complex for atomization.

These and other embodiments can optionally include one or more of the following features. The method can include filtering both the liquid fragrance oil in the reservoir assembly and the collected oil from the atomizer complex that drained down the drainage tube, and suctioning, with the vacuum tube, both the filtered liquid fragrance oil and the filtered collected oil back into the atomizer complex for atomization. The method can include suctioning and then filtering both the fragrance oil in the reservoir assembly and the collected oil from the atomizer complex that drained down the drainage tube. The method can include suctioning and filtering only the fragrance oil in the reservoir assembly that excludes the collected oil from the atomizer complex that drained down the drainage tube. The method can include storing a supply of the liquid fragrance oil for the scent delivery system in the reservoir assembly. The drainage tube can include the vacuum tube inside of the drainage tube that extends along a longitudinal length down the drainage tube, and the drainage tube can be configured to at least contact a level of the liquid fragrance oil in the reservoir assembly. The drainage tube and the vacuum tube can be arranged to extend along a longitudinal length down into the reservoir assembly. The drainage tube and the vacuum tube can be configured to at least contact a level of the liquid fragrance oil in the reservoir assembly. The method can include constantly recirculating the oil between the atomizer complex and the reservoir assembly so that the oil remaining in the reservoir assembly is constantly filtered, where the constantly recirculated oil may exclude the atomized liquid fragrance oil that is delivered into the air as the scented mist. The method can include separating a first mixture of oil inside the drainage tube from the liquid fragrance oil in the bottle. The method can include generating a path for a second mixture of liquid oil located above a filter housing to travel underneath the filter housing and to be filtered by a filter screen before being suctioned into the vacuum tube. The second mixture of liquid oil above the filter housing can include non-atomized liquid oil and the collected oil. An area near a terminal end of the drainage tube can include the filter screen or a semipermeable membrane inside of the drainage tube, where the filter screen can be covered by the filter housing. The filter screen or the semipermeable membrane can separate the first mixture of oil inside the drainage tube from the liquid fragrance oil in the bottle. The method can involve equalizing a first pressure in the drainage tube with a second pressure in the reservoir assembly with one or more pressure equalization holes in the drainage tube. The method can involve utilizing a funnel-shaped structure located on the bottom area of the atomizer complex to use impaction to coalesce a first portion of atomized particles back into liquid form for forming the collected oil, where a second portion of the atomized particles can include the scented mist that is delivered to the air outside of the atomizer complex.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A and 1B illustrate an example of an implementation of a scent delivery system that includes a reservoir assembly for storing fragrance oil and an atomizer.

FIGS. 2A-2E illustrate an example of implementation of a scent delivery system that includes a reservoir assembly for storing fragrance oil and an atomizer complex.

FIGS. 2F-2H show various three-dimensional (3D) diagrams of the scent delivery system.

Like reference symbols in the various drawings indicate like elements.

DETAILED DESCRIPTION

Scent delivery systems can be developed to use a dry-air technology that releases a fragrance without sprays, or heated oils. The scent delivery systems produce no messy residue to stain or damage floors or merchandise, so that scents can be delivered in a clean, controlled way. The scent delivery systems may require very little to no maintenance, other than adding or exchanging liquids for scents when the system is low or empty of liquids.

An airblast venturi atomizing device generally uses a high velocity air stream to break up a liquid into small droplets which are small enough to "float" in the air (e.g., under 10 microns). However the process actually may create a broad spectrum of droplet sizes, and the largest droplets may be too large to be useful as output. Disclosed herein are systems and techniques for separating the particles of desirable size from those that are too large to be used as output.

In some systems, the amount of oil that is drawn through the atomizer and yet returns as liquid without escaping to the environment may be from 100 to 400 times the mass that exits the system as the desired fine particles. In such cases, a large volume of oil per hour of operation is broken up and exposed to an intense flow of air before coalescing again as bulk liquid and being reused. This process consequently encourages evaporation to act on the oil which, as detailed further below, includes constituents with different vapor pressures. In short, such systems may function as distillation apparatuses, separating out the more volatile components of the oil mixture, which generally have relatively high vapor pressures, while leaving the lower vapor pressure components behind. This causes a composition change of the oil mixture which may result in a change in the fragrance of the oil mixture. In addition, as the composition of the oil mixture changes, the viscosity also may increase, becoming thicker over time. Such an increase in viscosity may decrease the efficiency of the atomization, compounding the issue of fragrance change with a decrease in fragrance intensity.

Collecting oil that passes through a venturi atomizer without escaping and returning it as liquid to be re-atomized as described herein may concentrate the effects noted above on a smaller volume of oil so that the properties of the bulk oil in the reservoir assembly are less affected over time, and the behavior of the machine is more consistent.

Referring to FIGS. 1A and 1B, an implementation of a scent delivery system 100 includes a reservoir assembly 105 for storing fragrance oil 110 and an atomizer 115. A vacuum tube 120 draws fragrance oil 110 from the reservoir assembly 105 into the atomizer 115. The atomizer 115 then converts the fragrance oil 110 into a scented mist 125 that is delivered into an airstream. Oil that is drawn into the atomizer 115 by the vacuum tube 120 but that is not ultimately atomized is collected in the atomizer 115 and returned to the vacuum tube 120 by a drainage tube 130 rather than being drained directly back into the reservoir assembly 105.

Generally, the oil that is drawn into the atomizer 115 by the vacuum tube 120 but that is not ultimately atomized includes a higher percentage of heavy (larger) odor notes than light (smaller) odor notes. As a result, if the oil that is not atomized and that is collected in the atomizer 115 drains directly back into the reservoir assembly 105, the concentration of heavy odor notes relative to the concentration of light odor notes in the oil remaining in the reservoir assembly 105 may increase over time. Consequently, the scent delivered by the scent delivery system 100 may change over time.

As compared to allowing the oil that is not atomized to drain back into the reservoir assembly, returning the oil that is not atomized to flow through the vacuum tube 120 increases the likelihood that the heavy odor notes within the returned oil will be atomized. As a result, the concentration of heavy odor notes relative to the concentration of light odor notes in the oil remaining in the reservoir assembly 105 may stay more steady over time, thereby leading to the delivery of a more uniform scent over time. Furthermore, returning the oil that is not atomized to the vacuum tube 120 may preserve the presence of light odor notes within the system over a longer period of time while also slowing the overall consumption of oil by the system over time.

Figure 1A:
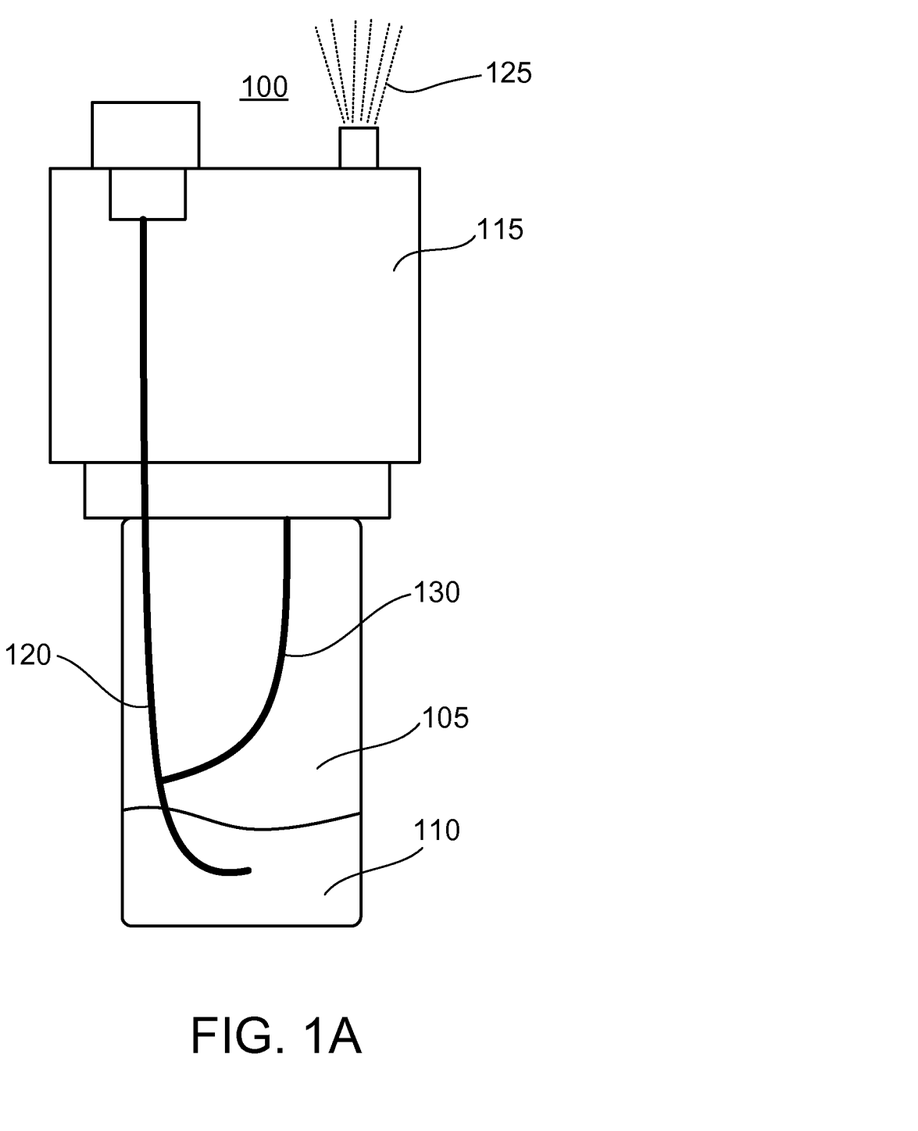
Figure 1B:
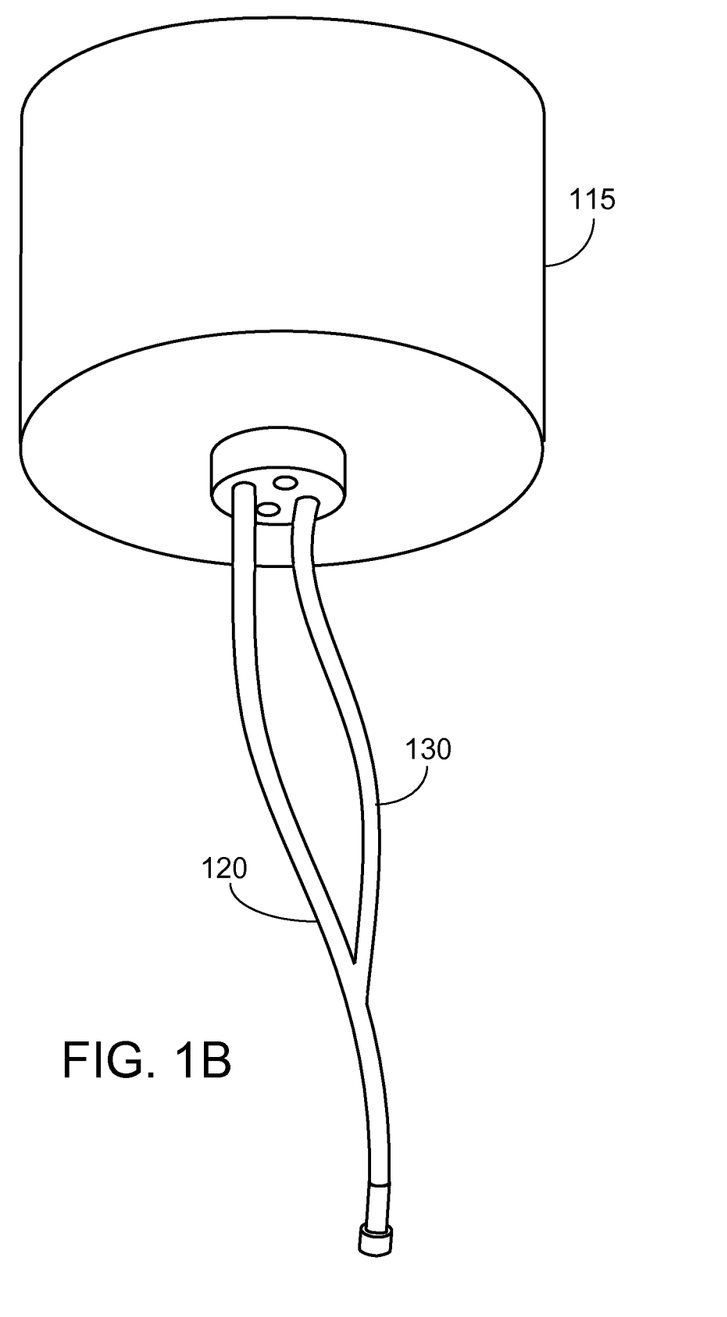
Figure 2A:
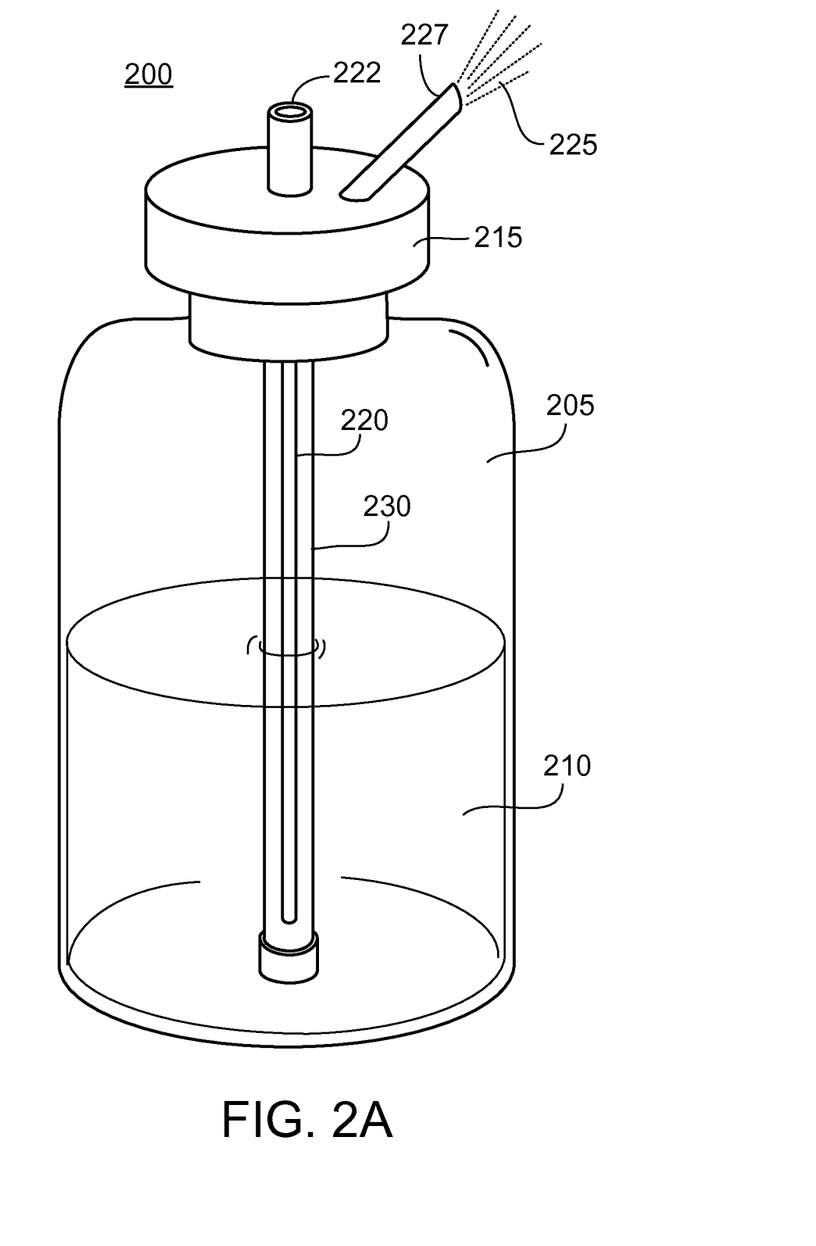
Figure 2B:
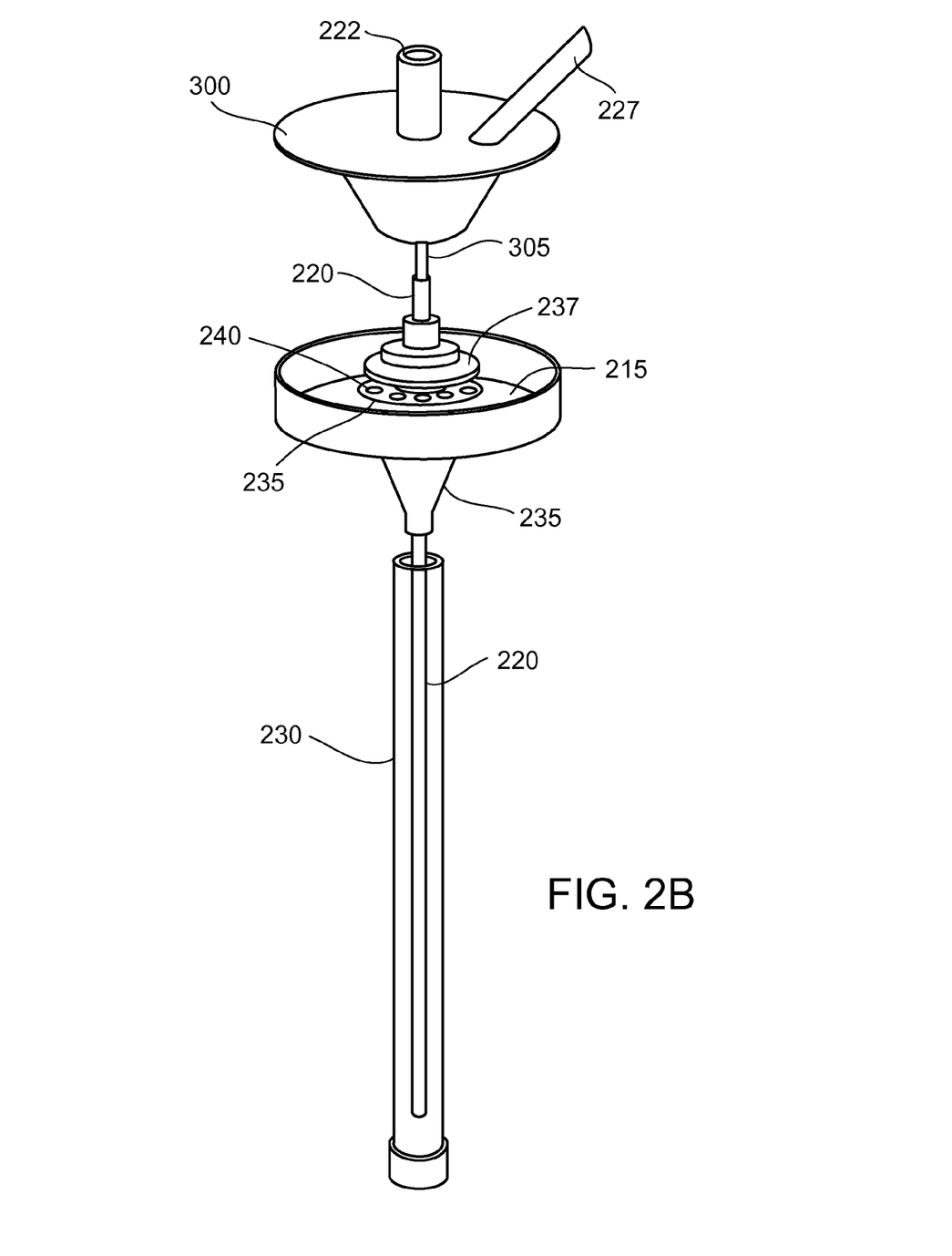

Referring to FIGS. 2A-2D, an implementation of a scent delivery system 200 includes a reservoir assembly 205 for storing fragrance oil 210 and an atomizer complex 215. As with the scent delivery system 100 illustrated in FIGS. 1A and 1B, a vacuum tube 220 draws fragrance oil 210 from the reservoir assembly 205 into the atomizer complex 215, where the atomizer complex 215 converts the fragrance oil 210 into a scented mist 225 that is delivered into an airstream by an output nozzle 227. In particular, as described in greater detail below, pressurized air (e.g., 10 psi) is injected into the atomizer complex 215 through air inlet structure 222, which is formed in the top portion 300 of the atomizer complex 215. Inlet structure 222 leads to a venturi chamber formed within the top portion 300 of the atomizer complex 215. In addition, vacuum tube 220 is coupled to an oil intake assembly 305 that also leads into the venturi chamber. The injection of pressurized air through air inlet structure 222 generates a low pressure area within the venturi chamber formed in the top portion 300 of the atomizer complex 300. This causes fragrance oil 210 to be drawn up through vacuum tube 220 into the venturi chamber, where the flow of pressurized air is used to atomize the fragrance oil 210. As illustrated in FIGS. 2A and 2B, the vacuum tube 220 is encased within a tube 230. As also will be described in greater detail below, tube 230 serves to collect atomized fragrance particles that are too large to be used for useful output as well as to drain excess oil that has collected in atomizer complex 215 back to the intake of the vacuum tube 220 where it again may be drawn up into the atomizer.

Referring specifically to FIG. 2B, a funnel-shaped structure 235, within which round holes 240 are defined, is incorporated within the atomizer complex 215. In addition, a collar 237 is formed over funnel-shaped structure 235, and vacuum tube 220 is threaded through the funnel-shaped structure 235 and its collar 237. Tube 230 is configured to surround the vacuum tube 220 and to receive the tapered end of the funnel-shaped structure 235 such that the tapered end of the funnel-shaped structure 235 fits securely within the tube 230. Excess oil that collects within the atomizer complex 215 drains out of the atomizer 215 through round holes 240 and into the funnel-shaped structure 235. From the funnel-shaped structure 235, the oil drains into tube 230, where it is drained around the outside of the vacuum tube 220 and ultimately returns to the intake of the vacuum tube 220.

Figure 2C:
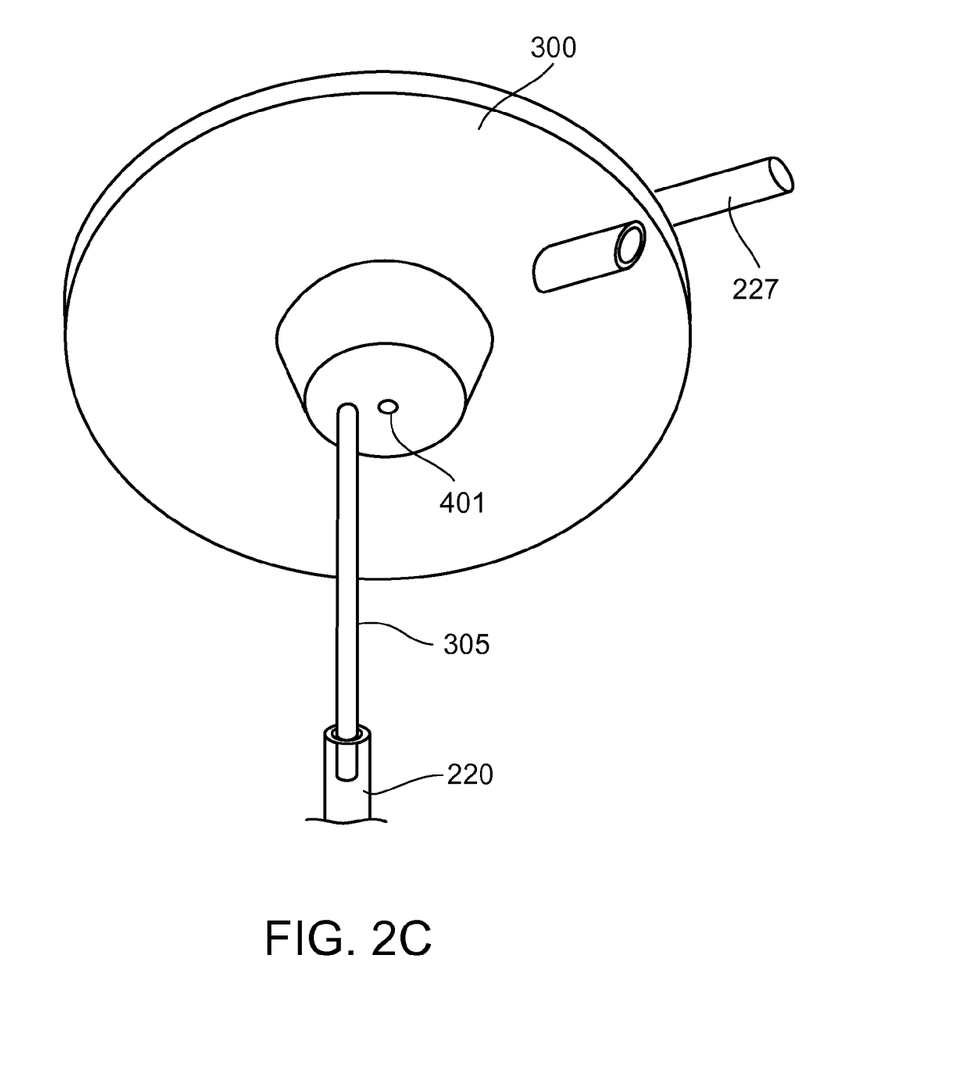

Referring to FIG. 2C, the underside of the top portion 300 of atomizer complex 215 is illustrated. As illustrated in FIG. 2C, the top portion of the atomizer complex 215 includes a structure inside of which the venturi chamber is formed. As described above, inlet structure 222 leads to this venturi chamber as does oil intake assembly 305. Pressurized air is injected into the venturi chamber through inlet structure 222, resulting in a low pressure area within the venturi chamber that causes oil to be drawn into the venturi chamber through vacuum tube 220 and oil intake assembly 305. When the oil enters the venturi chamber, it is subjected to the pressurized air flow, which serves to atomize the oil into a mist that is then discharged through orifice 401. As described above, the mist that is discharged through orifice 401 may include particles of various different sizes, some of which are suitable for output and others of which are too large to be used as output.

The separation of small airborne particles from big ones may be accomplished though impaction. Systems disclosed herein may make use of physical impaction where the larger particles are directed towards a solid surface and crash into it as their momentum is high enough to overcome the resistance of the stationary air adjacent to the surface. For example, in some implementations, physical impaction may be achieved by forcing the airstream with entrained particles to go around tight bends and corners, or though small holes. This method may tend to expose the stream of entrained particles to a lot of surfaces.

As will be described in connection with FIGS. 2D and 2E below, systems disclosed herein also may make use of virtual impaction, in which the momentum of the larger particles serves to carry them out of a moving airstream so that the smaller particles follow the moving air while the larger ones follow a different path or simply fall in relatively still air.

Referring to FIG. 2D, funnel shaped assembly 235 with tube 230 attached is in operating alignment with the airblast atomizer which is discharging a mist downwards from orifice 401. Vacuum tube 220 is not shown in FIG. 2D to focus on the outgoing flow.

Arrow 406 shows the path of the initial spray of atomized liquid particles from orifice 401 moving at relatively high velocity. Some of these particles, especially the larger ones, collide with the interior wall of hollow cylindrical section 404 formed in the funnel-shaped assembly 235 as well as the interior walls of the funnel-shaped section of funnel-shaped assembly 235. These collisions generally coalesce these particles back into bulk liquid which runs and drips to the bottom of tube 230. The path of the airflow through the device is shown by arrows 408, which turns and flows upwards though the holes 240 carrying with it the entrained aerosol particles of desirable small size. These particles then enter the interior of the atomizer complex 215 and are discharged through nozzle 227. Arrow 407 shows the path of larger particles from orifice 401 that have sufficient momentum to be carried out of the airflow in funnel shaped assembly 235. These larger particles are more likely to collide with the surface of tube 230 than they would be to escape with airstream 408 through round holes 240, though some of the larger particles still may escape with airstream 408 through round holes 240. Pressure equalization holes 409 may be formed in tube 230 or assembly 235 to equalize pressure in tube 230 with that in reservoir assembly 205 (e.g., so that the fluid level in tube 230 will match closely that of reservoir assembly 205 regardless of air flow introduced from orifice 401). When such pressure equalization holes 409 are formed, they generally are formed at locations above the level of oil in reservoir assembly 205.

Permeable separator 410 separates the contents of tube 230 from the fragrance oil 210 in reservoir assembly 205. Vacuum tube 220 conveys liquid from the bottom of tube 230 just above separator 410. In operation the liquid atomized though orifice 401 that does not exit the system through nozzle 227 will be collected in tube 230 and returned via tube 220 with minimal mixing with the contents of reservoir assembly 205. As fragrance oil of the proper particle size exits the device, fresh oil will pass into tube 230 through permeable separator 410 to maintain substantially equal hydraulic pressure on both sides of separator 410 (and thus equal fluid levels in tube 230 and reservoir assembly 205). Permeable separator 410 may occlude the terminal end of tube 230 or the end of vacuum tube 220 or both simultaneously. The function of separator 410 could as a further alternative be performed by 2 separate pieces, one to screen the oil moving up vacuum tube 220 and the other to restrict the diffusion of oil between tube 230 and reservoir assembly 205 as described above. In some implementations, separator 410 is a fine mesh plastic screen. Alternatively, many other permeable materials such as, for example, felt also may be used for separator 410.

Figure 2D:
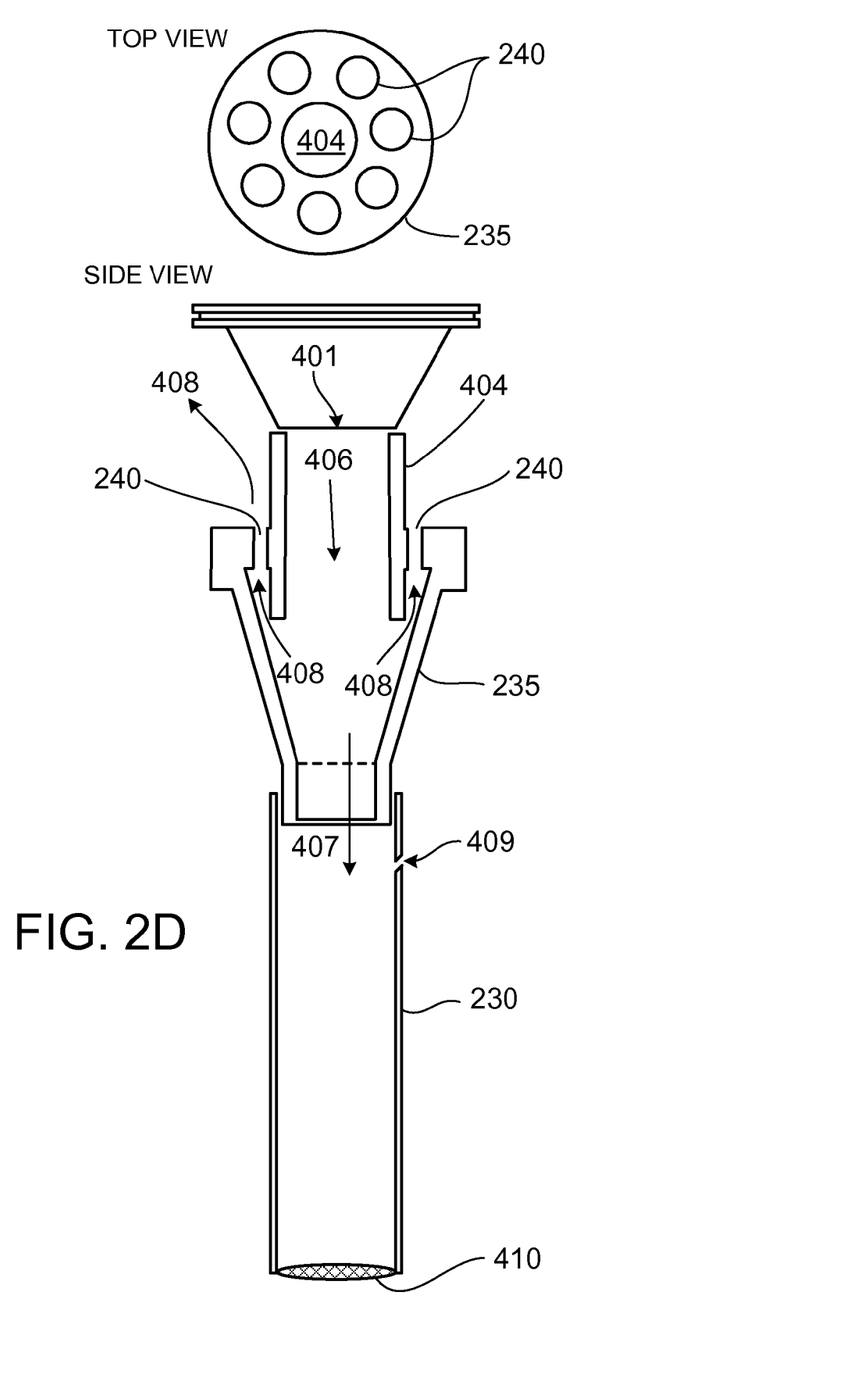

Round holes 240 also allow liquid fragrance oil that has coalesced further along the fragrance delivery path (e.g., within the interior of atomizer housing 215) to drain back to tube 230. Round holes 240 and the gap between the bottom of cylindrical section 404 and the funnel shaped wall of funnel-shaped structure 235 both also serve to act as physical particle impactors removing some of the larger particles from the airstream. As illustrated in FIGS. 2B and 2D, multiple round holes 240 are used, but an annular slot or other single opening or combinations of openings may be used in addition or as an alternative. In addition, in some implementations, funnel-shaped structure 235 may be replaced with nested box sections or concentric rings creating a similar airflow pattern. Furthermore, separate drainage and airflow paths could be employed as an alternative.

As fragrance oil may be strong smelling, messy, and persistent, features may be included within the atomization system to minimize the chances of spilling significant quantities of the fragrance oil. Such enhancements may enable the disclosed systems to be oriented horizontally or in an inverted fashion without causing the fragrance oil to pour out of the system. For example, in some implementations, pressure equalization holes 409 may be replaced with a valve that is configured to seal when the system tips beyond a threshold degree away from vertical. The sealing could be achieved with a moving weight, or it can be mechanically actuated by an external plunger.

In the event that the air pressure supply to the atomizer is switched on and off over time, the oil in vacuum tube 220 that has been suctioned above the level of the oil in the reservoir assembly 205 may fall back down each time the system switches off This may cause some of the oil in tube 230 to be displaced and mix with the bulk oil in the reservoir assembly 205. Likewise, when oil is suctioned back up tube 230, some fresh oil may be drawn into tube 230. Over many cycles this may cause considerable mixing. In order to mitigate this mixing, in some implementations, tube 230 may be sealed at the bottom so that no (or little) diffusion takes place between the oil in the main reservoir assembly 205 and the partially 'spent' oil in tube 230. Additionally or alternatively, tube 230 may be refilled with fresh oil on an as-needed basis. In some implementations, a one way valve between the two chambers 205 and 230 is used as a refilling mechanism. Alternatively, in some implementations, an active sensor may be used to pump in oil when tube 230 is determined to be empty of re-circulating oil. The active sensor may detect the level of liquid in tube 230 or, alternatively, it may detect the failure of the atomizer to produce mist while active.

In some implementations, tube 220 may be run in parallel to rather than inside tube 230. This may minimize interference with the mist discharged through orifice 410. In addition, running vacuum tube 220 outside of tube 230 may also allow for easier assembly with a filter on the end of the vacuum tube 220. In such implementations, a combination filter of porous plastic may simultaneously serve to filter the liquid moving up the vacuum tube 220 and perform the permeable barrier function of part 410.

Figure 2E:
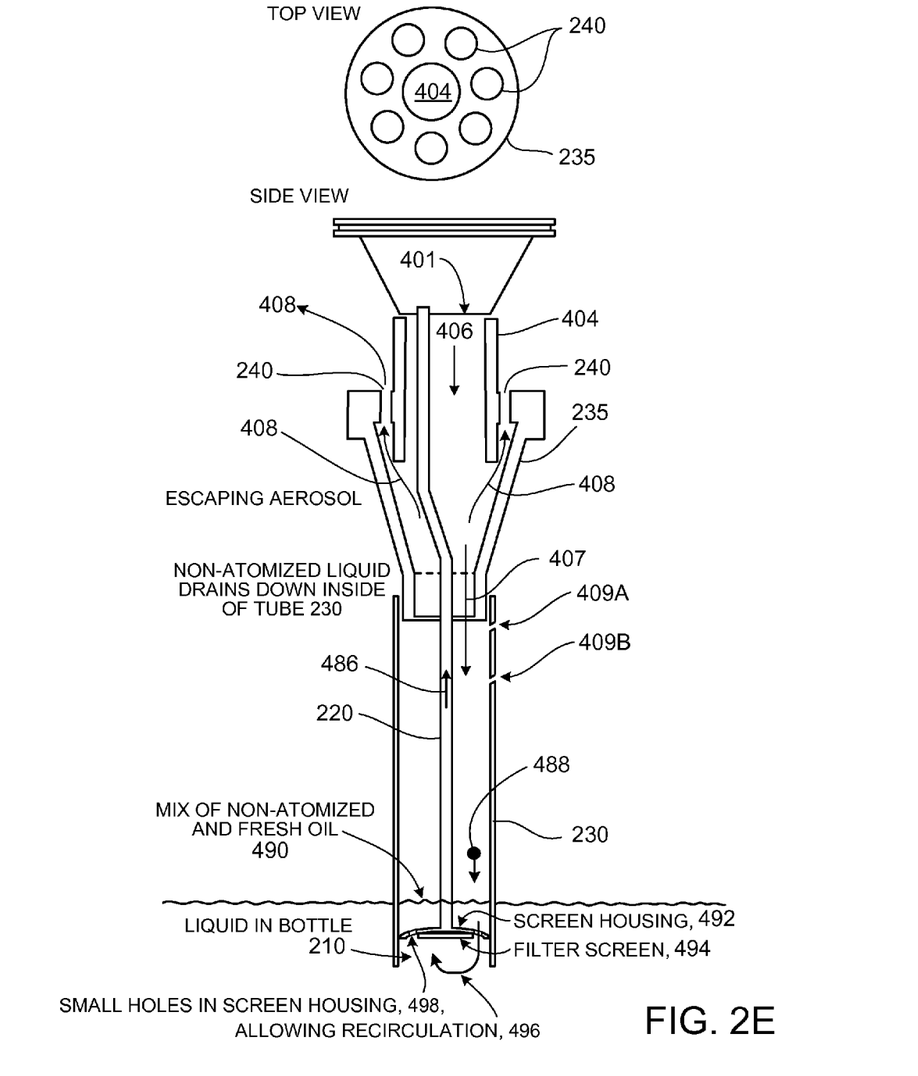

FIG. 2E shows another example of an implementation of the scent delivery system. In FIG. 2E, the funnel shaped assembly 235 with the tube 230 attached operates with the airblast atomizer that discharges a scented mist from orifice 401. While some features differ, several features of FIG. 2E may be similar to corresponding features of FIG. 2D.

FIG. 2E shows the vacuum tube 220. As described above, pressurized air is injected into the venturi chamber through inlet structure 222, resulting in a low pressure area within the venturi chamber that causes oil to be drawn into the venturi chamber through vacuum tube 220 and oil intake assembly 305. Arrow 486 shows the flow through the vacuum tube 200.

Oil 210 is located in the bottle outside of the tube 230, and a mixture 490 of non-atomized and fresh oil 490 is located inside the tube 230. The terminal end of the vacuum tube 220 includes a screen housing 492 and a filter screen 494 that are both located below the level of the oil 210 in the bottle. The terminal end of the vacuum tube 220 may be coupled with the screen housing 492 and/or the filter screen 494, and the vacuum tube 220 has an opening to suction in the oil from underneath the screen housing 492 and the filter screen 494. The filter housing 492 has small holes 498 to allow for the recirculation of oil 488 that comes down from inside the walls of the tube 230 as shown at arrow 496. The oil 488 that comes down the side of the tube 230 may be oil that has recently been atomized and condensated, non-atomized oil from the orifice 401, or more generally, oil 488 that has recently come from the orifice 401 and/or the funnel shaped assembly 235. This oil 488, which sometimes may be referred to as recently-used oil, recently-atomized oil, non-atomized oil, or oil condensate, may be generally be referred to as "collected oil" 488. The collected oil 488 can be drawn into the into the mixture 490 of non-atomized and fresh oil, which then can be drawn into the small holes 498 in the filter housing 498, to be sucked up into the vacuum tube 220 to be atomized. In this respect, the flow of the collected oil 488 can be recirculated to be re-atomized.

In FIG. 2E, the lower walls of the tube 230 are extend below the level of the liquid in the reservoir assembly 205. In some implementations, for example, the lower walls of the tube 230 may extend at least a few millimeters (e.g., 2-3 millimeters) below the level of the liquid in the reservoir assembly 205. In some embodiments, the tube 230 may extend considerably beneath the level of the liquid when the bottle is full. In some embodiments, the tube 230 may extend to (or nearly to) the bottom of the reservoir assembly 205, which can allow the system to run until reservoir assembly 205 is emptied, and can allow for the separation of the mostly fresh oil and the collected oil 488 until the reservoir assembly 205 is emptied. The lower walls of the tube 230 can separate the oil 210 in the bottle from the mixture 490 of non-atomized and fresh oil inside of the tube 230, so that the oil 210 in the bottle outside of the lower walls of the tube 230 may not readily mix with the mixture 490 of non-atomized and fresh oil inside of the tube 230. In this implementation, the mixture 490 of non-atomized and fresh oil inside of the tube 230 can have an easier path in being suctioned through the filter screen 494 and to the tube 220 when compared to the oil 210 inside of the reservoir assembly that is outside of the tube 230. The constant addition of collected oil 488 to the interior volume of tube 230 can lead to a flow of this collected oil downward though the holes 498. This can cause the oil that is suctioned up tube 220, which is all filtered though screen 494, to primarily include collected oil 488 passing down though the holes 498, where only a very small proportion of the oil that is suctioned up tube 220 is fresh oil.

In some implementations, the filter screen 494 may have small holes or one-way valves to filter the (recirculated) oil and allow the oil to be suctioned up into the tube 220. Because the collected oil 488 is constantly being recirculated throughout the scent delivery system 200, the oil can stay fresher longer, and the oil does not have to go from the atomizer and back into the entirety of reservoir assembly 205 to freely and completely mix with the older oil, for which the composition and scent of the oil 210 in the reservoir assembly 205 would change more quickly over time.

In some implementations, for example, the collected oil 488 (or the mixture 490) can accumulate in the bottom of the tube 230 and can be recirculated by passing through small holes 498 in the screen housing 492 that may be approximately 0.060" in diameter, for example. Other hole sizes may be implemented in the screen housing 492 and/or the filter screen 494. In some implementations, the small holes 498 may be one-way valves that permit an oil flow such that the oil can only be suctioned into the tube 220 in a direction towards the atomizer complex 215. The small holes 498 or one-way valves at the bottom of the tube 230 may reduce an amount of mixing between the mixture 490 inside of the tube 230 and the oil 210 outside of the tube 230.

As the level of c rises inside tube 230, it may displace some of the liquid through the small holes 498, at which point the suction though the filter screen 494 draws this oil back up to the atomizer complex 215. Because the collected oil 488 (e.g., previously-atomized oil, oil condensate) may contain many entrained air bubbles, it can be lighter than the oil 210 surrounding it in the bottle, may float or rise on top of the other oil, and thereby can be more readily recirculated, rather than just mixing with the oil 210 in the bottle. For example, the collected oil 488 may appear frothy and may float momentarily before mixing in the mixture 490. In some implementations, most of the mixture 490 in the tube 230 may be collected oil 488, which will be recirculated to be re-atomized again. The oil inside of the tube 230 can be progressively distilled over time.

The implementation of FIG. 2E can provide filtering for the collected oil 488 at a higher rate when compared to an implementation that does not recirculate the collected oil 488 primarily. Also, when the oil level is low in the reservoir assembly 205, the pressure may be low and, consequently, there may not be much pressure to push the oil throughout the scent delivery system 200. In the implementation of FIG. 2E, the collected oil 488 can be constantly pushed through the system and filtered through the filter screen 494, even when the oil level (and/or pressure level) is low in the reservoir assembly 205. In some implementations, the oil feeding the atomizer complex 215 through the tube 220 may always be filtered by the filter screen 494 at the bottom of the tube 220.

Two pressure equalization holes 409A, 409B are in FIG. 2E in tube 230 (or alternatively assembly 235) to equalize pressure in the tube 230 with the pressure in the reservoir assembly 205 (e.g., so that the fluid level in tube 230 will match closely the fluid level of the reservoir assembly regardless of air flow introduced from orifice 401). When such pressure equalization holes 409A, 409B are formed, they generally are formed at locations above the maximum level of oil that should exist in reservoir assembly 205. Two pressure equalization holes 409A, 409B allows air to flow into and out of the tube 230 or assembly 235. In other implementations, more than two pressure equalization holes may be positioned above the maximum fill fluid level of the reservoir assembly 205. Some of these implementations may provide an escape path for oil and return path for air inside the bottle in the event that the bottom of the tube cannot allow oil to escape, such as for the case of an intentional or accidental one way valve, for example. Some of these implementations may provide an escape path and a return path for air inside the bottle. The filter screen 494 can constantly filter out larger particles or undesired particles in the oil before the oil is sent into the tube 220, which thereby can enhance the length of the operation of the scent deliver system.

Figure 2F:
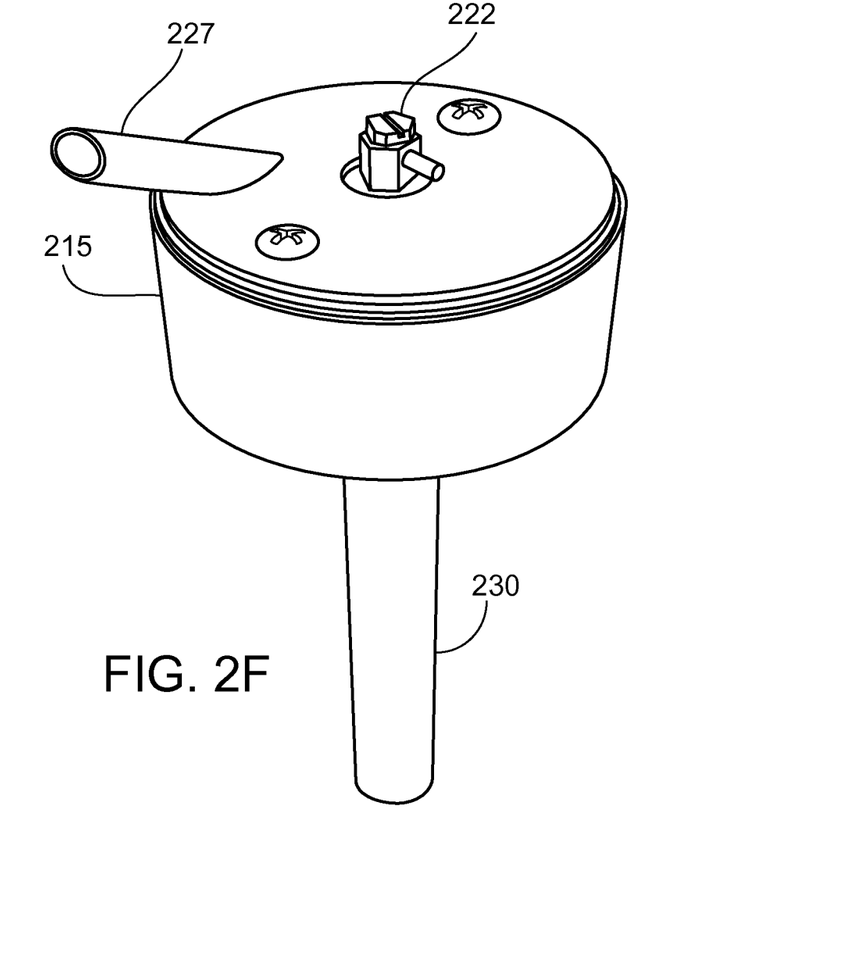
Figure 2G:
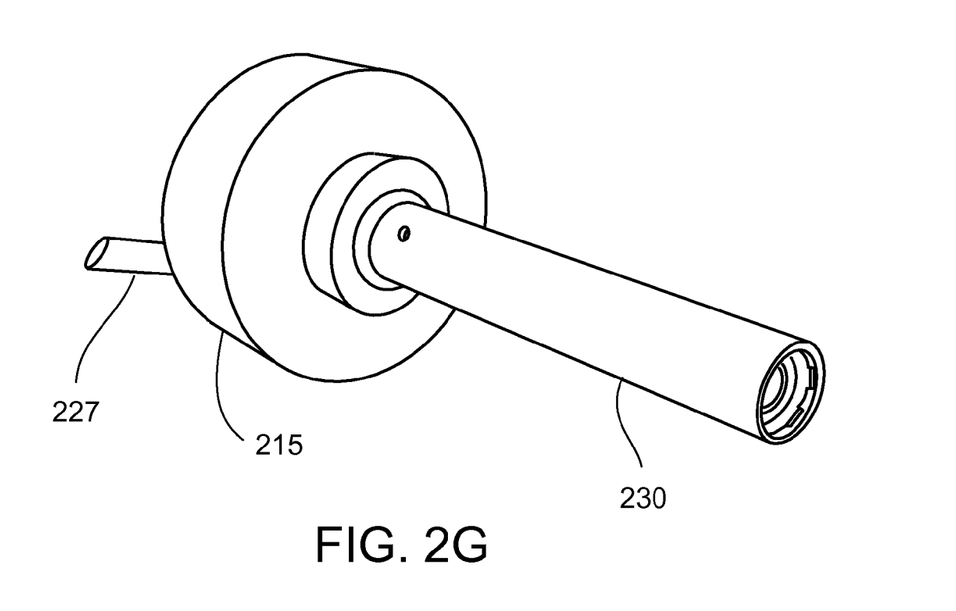
Figure 2H:
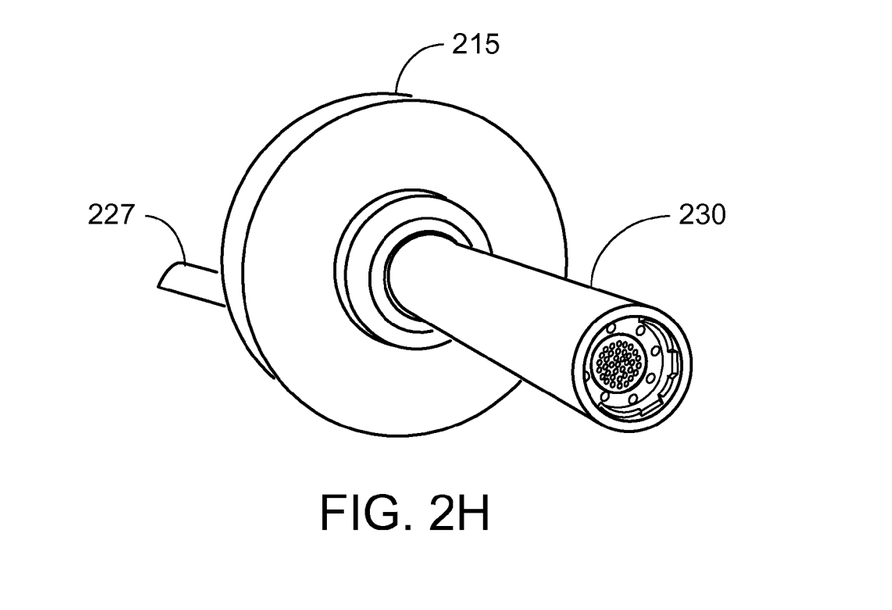

FIGS. 2F-2H show various three-dimensional (3D) diagrams of the scent delivery system. In the implementation of FIGS. 2F-2H for the scent delivery system 200, an atomizer complex 215 is shown with an output nozzle 227 and an air inlet structure 222. The atomizer complex 215 has a tube 230 that encloses a vacuum tube 220 (not shown). A permeable separator 410 can separate the contents of tube 230 from the fragrance oil 210 in reservoir assembly.

Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

A number of embodiments of the invention have been described. Nevertheless, it will be understood that various modifications may be made without departing from the spirit and scope of the invention. Accordingly, other embodiments are within the scope of the following claims.

What is claimed is:
1. A scent delivery system comprising:
  a reservoir, the reservoir comprising a liquid fragrance oil;
  an atomizer, the atomizer comprising:
    a chamber;
    an air inlet structure, wherein the chamber is in fluid communication with an exterior of the atomizer through the air inlet structure; and
    an oil intake;
  a vacuum tube comprising a first end and a second end, the first end coupled to the oil intake and the second end extending into the reservoir below a level of the liquid fragrance oil wherein the oil intake is positioned between the chamber and the vacuum tube, and wherein the chamber is in fluid communication with the vacuum tube through the oil intake; and a drainage tube in fluid communication with the atomizer and extending from the atomizer into the reservoir, wherein one end of the drainage tube is coupled to the vacuum tube to enable oil drainage into the reservoir through the second end of the vacuum tube.

2. The scent delivery system of claim 1, further comprising a drainage apparatus coupled to the atomizer and comprising the drainage tube, wherein the drainage apparatus comprises an opening to the reservoir positioned above the level of the liquid fragrance oil.

3. The scent delivery system of claim 2, wherein the opening is in a sidewall of a drainage tube of the drainage apparatus.

4. The scent delivery system of claim 2, wherein the drainage apparatus comprises a funnel-shaped structure positioned between the drainage tube of the drainage apparatus and the atomizer, and wherein the opening is in the funnel-shaped structure.

5. The scent delivery system of claim 2, wherein the drainage apparatus also comprises a second opening to the reservoir.

6. The scent delivery system of claim 2, wherein the atomizer is configured to:

draw in a drawn-in portion of the liquid fragrance oil from the reservoir through the vacuum tube;

atomize the drawn-in portion of the liquid fragrance oil into a scented mist;

deliver a first part of the scented mist to air outside of the atomizer;

collect a second part of the scented mist that is not delivered to the air outside of the atomizer; and return the collected second part of the scented mist to the reservoir.

7. The scent delivery system of claim 6, wherein the drainage apparatus comprises a funnel-shaped structure positioned between the drainage tube of the drainage apparatus and the atomizer, and wherein the funnel-shaped structure is configured to impact the scented mist to coalesce the second part of the scented mist to be returned to the reservoir.

8. The scent delivery system of claim 2, wherein the drainage apparatus comprises a funnel-shaped structure positioned between the drainage tube of the drainage apparatus and the atomizer, and wherein the funnel-shaped structure comprises a tapered end that extends into the drainage tube.

9. The scent delivery system of claim 2, wherein the chamber comprises a first area and a second area, and wherein a first pressure at the first area is lower than a second pressure at the second area to suction the liquid fragrance oil into the chamber from the reservoir through the vacuum tube.

* * * * *